US012624325B2

(12) United States Patent
Bendall et al.

(10) Patent No.: US 12,624,325 B2
(45) Date of Patent: May 12, 2026

(54) SINGLE-USE CONTAINER WITH 3D PRINTED FUNCTIONAL ELEMENT, PRINTING METHOD THEREFOR AND ASSEMBLY

(71) Applicant: Sartorius Stedim FMT S.A.S., Aubagne Cedex (FR)

(72) Inventors: Richard Bendall, Gloucestershire (GB); Jeremy Pullin, Bristol (GB); Isabelle Gay, Peypin (FR)

(73) Assignee: Sartorius Stedim FMT (FR)

( * ) Notice: Subject to any disclaimer, the term of this patent is extended or adjusted under 35 U.S.C. 154(b) by 1017 days.

(21) Appl. No.: 17/292,416

(22) PCT Filed: Oct. 22, 2019

(86) PCT No.: PCT/EP2019/078722
§ 371 (c)(1),
(2) Date: May 7, 2021

(87) PCT Pub. No.: WO2020/094391
PCT Pub. Date: May 14, 2020

(65) Prior Publication Data
US 2022/0010253 A1     Jan. 13, 2022

(30) Foreign Application Priority Data

Nov. 9, 2018    (EP) .................................... 18290131

(51) Int. Cl.
*C12M 1/00*          (2006.01)
*B29C 64/118*        (2017.01)
(Continued)

(52) U.S. Cl.
CPC ........... *C12M 23/28* (2013.01); *B29C 64/118* (2017.08); *B29C 64/245* (2017.08); *B29C 64/35* (2017.08);
(Continued)

(58) Field of Classification Search
CPC ...... A61J 1/10; A61J 2200/40; A61J 2200/70; A61J 2205/30; B29L 2131/7148; C12M 23/14; C12M 23/28
See application file for complete search history.

(56) References Cited

U.S. PATENT DOCUMENTS 6,183,460 B1 * 2/2001 Smith ....................... A61J 1/10
                                                              604/408
2015/0132491 A1 * 5/2015 Levine ................... B33Y 10/00
                                                              427/258
(Continued)

FOREIGN PATENT DOCUMENTS

EP        3 078 735 A1    10/2016
JP        2017528347 A     9/2017
(Continued)

OTHER PUBLICATIONS

International Search Report and Written Opinion, mailed Jan. 17, 2020, issued for International Application No. PCT/EP2019/078722, 9 pages.

*Primary Examiner* — Jill A Warden
*Assistant Examiner* — Dwayne K Handy
(74) *Attorney, Agent, or Firm* — Klarquist Sparkman, LLP

(57) ABSTRACT
A method for producing a single-use container, particularly a single-use bioreactor, an assembly system, and a single-use container particularly a single-use bag such as a single-use bioreactor comprising: a base material; and at least one functional element being at least partially connected with the base material, wherein the functional element is obtained by a three dimensional printing technique from at least one printable material, wherein the printable material is heated during the three dimensional printing thereby at least partly connecting the printed functional element to the base material.

15 Claims, 6 Drawing Sheets

(51) Int. Cl.

| | |
|---|---|
| *B29C 64/245* | (2017.01) |
| *B29C 64/35* | (2017.01) |
| *B29C 64/357* | (2017.01) |
| *B33Y 10/00* | (2015.01) |
| *B33Y 30/00* | (2015.01) |
| *B33Y 40/20* | (2020.01) |
| *B33Y 80/00* | (2015.01) |
| *B29L 31/00* | (2006.01) |

(52) U.S. Cl.

CPC ............ *B29C 64/357* (2017.08); *B33Y 10/00* (2014.12); *B33Y 30/00* (2014.12); *B33Y 40/20* (2020.01); *B33Y 80/00* (2014.12); *C12M 23/14* (2013.01); *B29L 2031/7148* (2013.01)

(56) References Cited

U.S. PATENT DOCUMENTS

| | | | |
|---|---|---|---|
| 2016/0038655 A1* | 2/2016 | Weisman ................ | A61L 15/22 |
| | | | 425/375 |
| 2017/0151719 A1 | 6/2017 | Swartz et al. | |
| 2017/0191017 A1 | 7/2017 | Heinz et al. | |
| 2018/0117821 A1 | 5/2018 | Grifoni et al. | |
| 2018/0154573 A1 | 6/2018 | Miles | |
| 2018/0179486 A1 | 6/2018 | Fadell et al. | |

FOREIGN PATENT DOCUMENTS

| | | |
|---|---|---|
| JP | 2018034336 A | 3/2018 |
| WO | WO 2017/083705 A1 | 5/2017 |
| WO | WO 2017/139766 A1 | 8/2017 |
| WO | WO 2018/115081 A1 | 6/2018 |

* cited by examiner

SINGLE-USE CONTAINER WITH 3D PRINTED FUNCTIONAL ELEMENT, PRINTING METHOD THEREFOR AND ASSEMBLY

CROSS REFERENCE TO RELATED APPLICATIONS

This is the U.S. National Stage of International Application No. PCT/EP2019/078722 filed Oct. 22, 2019, which was published in English under PCT Article 21(2), which in turn claims the benefit of European Patent Application No. 18 290 131.4, filed Nov. 9, 2018. The prior applications are incorporated herein by reference in their entirety.

The invention relates to a single-use container, for example a single-use bioreactor, a method for producing this container and an assembly for producing items, particularly a single-use container and/or elements thereof. The invention is specifically related to the fields of biotechnology, bioprocessing, chemical and/or biological plant construction, food and beverage processing and/or chemical technology. The invention is particularly related to fluid management in biopharmaceutical industry.

In the production of items such as single-use containers, being comprised of single elements which are produced independently from each other, usually a production step of connecting single elements with each other is required, such as welding and/or gluing and/or mounting for example. Typically, elements comprise protruding portions and/or areas which extend from the main body of an element to provide a surface which may be an excess surface to which glue can be applied or at which a step of welding can be performed. In FIG. 1a, an example of a conventional production procedure is illustrated and discussed further below.

For example, EP1778828B1 discloses a bioreactor, comprising a reactor vessel embodied as a bag, wherein a receiving port is arranged at an upper side of the reactor bag and is provided with a flange piece tightly sealed to a vessel wall. A sensor piece is to be connected to the flange piece via a tubular connector piece in such a way that the sensor piece reaches into the reactant from above. Further, EP2707694A1 discloses a single-use bag having a flexible wall comprising a fixation flange for fixing a sensor head to the flexible wall of the single-use bag. The fixation flange may be set to the flexible wall by being adhesive-bonded, welded, screwed, clamped or latched thereto.

According to an aspect, there is a need for increasing the degree of versatility of a single-use container, a method for producing this container and an assembly for producing items, particularly in view of the number of materials which may be connected and the arrangement of functional elements on a single-use bag.

The problem is solved by the independent claims. Preferred embodiments are subject of the dependent claims.

The following aspects of the invention provide a single-use container, a method for producing this container and an assembly for producing items, such as a single-use container allowing multiple materials to be combined and/or connected. Further, the structures of the functional elements, as well as the arrangement on a single-use bag may be improved.

According to one aspect, there is provided a single-use container, for example a single-use bioreactor, comprising a base material, particularly a wall element and/or a wall and/or skin of the single-use container, particularly of a single-use bioreactor which may be a single-use bag, such as a foil, a thin sheet and/or a stock sheet; and at least one functional element, for example a port, a sensor holder, a sensor part or the like, being at least partially, preferably permanently connected with or to the base material, wherein the functional element is obtained by a three dimensional (3D) printing technique from at least one printable material, wherein the printable material and/or the base material is/are heated during printing thereby (so as to) at least partly connecting the printed functional element to the base material.

In other words, a single-use container, which may be a single-use bag, comprises at least two parts: One part, i.e. a base material, such as for example a stock material and/or a pre-made item and/or a pre-made bag or a pre-made part thereof. The base material being connected to or with at least one second part. The at least one second part is a functional element which particularly is produced by being printed directly onto the base material. At least a portion or a part of the functional element may be in direct contact with the base material being directly connected to the base material such that a physical contact is established. The connection of the two parts, i.e. the base material and the at least one functional element, is established during at least a part of time, i.e. a fraction of time or a period, needed for the production of the functional element performed by 3D printing and heating. It should be understood that the functional element may by 3D printed onto the base material in one step or in plural steps or stages particularly being separate in time. In other words, the functional element may be formed by subsequently 3D printing a sub-element on another sub-element previously 3D printed on the base material.

In other words, the single-use container comprises a base material and at least one functional element which is obtained from—or a product of a 3D printing from a printable material. The printable material preferably connects, particularly permanently with—and/or adheres to the base material, as the printable material is heated during the 3D printing and the heated printable material may polymerize and/or fuse and/or connect with at least part of the base material. Printable materials are heated during 3D printing processes, being referred to the "Material extrusion" group of printing techniques, such as FDM (fused deposition modeling) or FFF (fused filament fabrication).

The base material might be pre-heated by external means in order to reach the appropriate melting temperature of the interface for proper bonding with the 3D printed element. Pre-heating might be done, e.g. by blowing hot air onto the base material and/or use a heated plate as a conveyor belt and/or provide a heat radiation, respectively a thermal radiation, such as infrared radiation by a thermal radiation source, and then retaining the heat during the time of operation. Preferably, the base material is pre-heated. A permanent connection between two elements may be achieved by polymeric fusion of both elements at certain positions, such as a seam, upon heating the polymeric materials. Non-polymeric materials, such as metal ink may also be heated for application to the base material and for establishing an adhesion between the two elements, the base material and the functional element.

The fusion between the two parts or elements, the base material and the functional element, may particularly be established at the very moment when the first layer of the functional element is printed onto the base material. The temperature or amount of heat supply provided to the printable material and/or the base material may be maintained during the entire time of production or it may be varied, as required by the process.

The single-use containers advantageous, as one or several functional elements may be bonded at and/or on a base material and/or a pre-made bag in one single step of 3D printing. The 3D printing of functional elements substitutes for multiple production steps which are usually required during a conventional production procedure.

Further, a single-use container as described herein, which may be a single-use bag, comprises functional elements that do not necessarily require excess protruding portions, areas or surfaces sticking out from a functional element. Usually, when applying a conventional bonding technique, such as a welding step, a functional element requires an excess and/or protruding surface to be connected to the base material. Such surfaces, particularly excessive and/or protruding surfaces sticking out from the functional element might harm the base material, for example if the base material comprises a very thin and sensitive sheet layer. According to the production method described herein, typically no such excess and/or protruding surface sticking out from the functional element, is required and therefore, the possibility that the base material, such as a thin sheet, is damaged by the functional element is reduced or eliminated. Hence, the single-use container may comprise multiple functional elements being positioned close to each other. Delicate and/or fine and/or complex structures may also be easily applied as functional element(s), such as supporting ribs or reinforcement structures. A firm connection between the base material and the functional element ensures stability and safety, which allows uncomplicated handling for example with respect to shipping and transport of the item, i.e. the single-use container. This technique allows to integrate these massive functional elements to the single-use container that are extremely difficult to weld to thin plastic single-use container wall. Moreover, it would allow to keep only the single-use container wall material in contact with the biopharmaceutical solution contained in the bag, the 3D printed functional elements being bonded on the external surface of the container wall.

As a consequence, single-use containers may be provided with a higher spatial density of functional elements positioned thereon. In other words, there may be provided more functional elements having a smaller distance to each other on a smaller area of the base material, as opposed to conventional containers being produced with conventional techniques.

In addition, it may be avoided to use and or implement adhesive materials such as glue, which may chemically harm the materials, for example the base material. Also, it can be avoided that degradation of a glued seam occurs, as the connection may be seamless, particularly being fused connection.

Moreover, the single-use container may be produced in an efficient, particularly cost efficient and easy way, as multiple steps may be automated, simplified and reduced or even avoided to connect parts or elements.

Optionally, several functional elements may be produced wherein a first functional element is connected to the base material and a second functional element is connected to the first functional element. For example, a reinforcement structure and/or a pad and/or a supporting layer, acting as a first functional element, may be printed onto a base material. A handle, acting as a second functional element, may be printed onto a surface of the reinforcement structure and/or a pad and/or a supporting layer. It is self-evident that any two of the disclosed functional elements and/or more than two of the disclosed functional elements may be connected in this or in a similar way.

According to another alternative aspect, there is provided a single-use container, for example a single-use bioreactor, comprising a base material, particularly a wall element and/or a wall and/or skin of the single-use container, particularly of a single-use bioreactor which may be a single-use bag, such as a foil, a thin sheet and/or a stock sheet; and at least one functional element, for example a port, a sensor holder, a sensor part or the like, being at least partially, preferably permanently connected with or to the base material, wherein the functional element is obtained by a three dimensional (3D) printing technique from at least one printable material, wherein the printable material is printed by means of material jetting onto a base material to construct the at least one functional element.

Printing techniques which do not require heating during the printing process are considered as belonging to the "material jetting" group of printing techniques. A material jetting technique may for example comprise polyJet printing, aerosol jetting, and jetting by means of "Vat polymerisation", such as SLA (stereolithography) or DLP (digital light processing).

The material jetting technique is advantageous as no heat is supplied during the process of printing the functional element onto the base material. Bonding may be realized due to polymerisation between the components, i.e. the substance of the base material and the substance of the printable material.

Preferably, the base material is at least one out of: an essentially two dimensional film, i.e. a very thin layer or film, a stock sheet, a pre-cut bag, a pre-made bag, particularly a single-use bag, a wall element and/or skin of a bag or a container.

A single-use container comprising a base material, such as an essentially two dimensional film, a stock sheet, a pre-cut bag, a pre-made bag may be connected easily and reliably with a functional element, even though the base material itself is a very delicate material which can easily be damaged. As a single-use container may be intended for various single-use applications, cost efficiency and flexibility in the container configuration is of high importance.

It may be desired to print a very delicate and/or complex and/or fine functional element onto the base material, which may also be very delicate and/or sensitive. The single-use container according to this example may be produced in a simple way making it possible to easily handle the difficulties when producing and connecting such elements. Therefore, the single-use container of this example may be comprised of very fine structures and materials.

Providing pre-made base materials such as a pre-made bag acting as the SU bag can have the advantage that merely the functional element is printed onto the base material for completing the production. In other words, after the functional element has been printed onto the base material, the item, i.e. the bioreactor, particularly the SU bag, may be ready to be used. This possibility allows a very versatile production.

Preferably, the functional element comprises at least one out of: a flange, a port, an inlet/outlet point, a sensor holder, a sensor or a part of a sensor, a window or a window frame, a connector, a label and/or a label information, a substantially three dimensional text, e.g. a Braille text, a reference marker or fiducial, a three dimensional structure and/or a three dimensional pattern, particularly a stabilizing and/or stiffening and/or reinforcement element, a tube holder, a handle, a metallic element, i.e. a metal element, particularly an electronic component. In particular, a flange may be understood as any interface with the base material, such as an external or internal ridge and/or rim and/or lip, which is intended to be connected with another element, particularly a pipe and/or a tube and/or a container. A port may be understood as a passageway into the bag, e.g. be an inlet and/or outlet point.

A flange, a port, an inlet/outlet point, a sensor holder, a sensor or a part of a sensor, a window or a window frame, a sewer port, a connector and the like may be required at a single-use container for gaining access to the interior of the container and/or bag of the single-use container. This access may be a physical and/or an optical access. Providing a sensor allows to permanently and/or temporarily monitor processes inside the single-use container. By providing a port, an inlet/outlet point and the like, a temporary or permanent access can be established to reach the inside or the inner volume of the single-use container.

A holder or the like may be advantageous to equip the single-use container with cables, tubes, sensors and/or other equipment which can be held close to the single-use container in order to provide a well-arranged system for easy use.

A label and/or a label information, a reference marker or fiducial may be provided for noting information on the single-use container wall or to achieve an indication of a filling status, respectively. A reference marker on a base material may be used for indicating a position at which an element should be located and/or printed. A reference line on the base material may indicate where a cut should be placed in a further procedure step. In other words, reference markers or fiducials may be provided for supporting and/or aiding a step of cutting of the stock sheet into patterns which might be 3D printed for accurate assembly.

The addition of fiducial markings can increase the accuracy of the placement of features and/or functional elements. In comparison with conventional techniques, the application of fiducials can be easily achieved using a 3D printing technique according to the present disclosure. Applying fiducials by means of 3D printing can effectively reduce the number of components for downstream assembly processes A label and/or labelling information may also be a 3D printed label. In this case, it is possible to avoid for example the problem of migration or creeping of ink and/or adhesive materials as often occurring when labelling traditionally onto the single-use container wall.

A three dimensional structure and/or pattern, particularly a stabilizing and/or stiffening and/or reinforcement element can provide an improved stability of the base material. A pattern and/or a reinforcement structure and/or a pad and/or a supporting sheet may be printed directly onto the base material. A further functional element such as a handle, a flange or a holder for a cable and/or sensor and/or tube may be printed onto the pattern and/or a reinforcement structure and/or a pad and/or a supporting sheet. This has the advantage of providing a more stable structure which is more resistant to degradation or damage. It may be particularly helpful if the base material is very sensitive and/or fragile and/or delicate, or to help the single-use container installation into stainless steel support container.

At least one reinforcement structure may also be provided at, particularly along edges of a SU bag or on the bottom of a SU bag to support the stability, particularly in a filled state. It might be possible that the SU bag would not maintain the shape in the filled state, such that a reinforcement structure would be necessary to provide a stable shape.

Preferably, the base material and/or the functional element and/or a printable material, from which the functional element and/or the base material is at least in parts composed, is at least partially composed from at least one of: PE (Polyethylene), PP (Polypropylene), PC (Polycarbonate), TPE (Thermoplastic Elastomer), EVA (Ethylene-vinyl acetate), Fluoropolymers, PET (Polyethylene terephthalate), POM (Polyoxymethylene), ABS (Acrylonitrile butadiene styrene), PLA (Polylactic acid), PA (Polyamide), PSU (Polysulfone), PES (Polyether sulfone), PEEK (Polyether ether ketone), Copolyesters, PMMA (Poly(methyl methacrylate)), PEI (Polyethylenimine), PPO (poly(phenylene oxide)), PS (polystyrene), PTFE (Polytetrafluoroethylene), PU (Polyurethane), silicone, acrylics (e.g. acrylic resins), composites resins with fillers (e.g. PLA with glass fibers), any new material, which is developed and qualified as suitable for medical, pharmaceutical and biopharmaceutical applications, and composite materials out of at least one of the above mentioned materials. Alternative possible materials are HDPE (high-density polyethylene), LLDPE (linear low-density polyethylene), LDPE (low-density polyethylene), PVC (Polyvinyl chloride).

Functional elements which are not intended to be in contact with the inner volume of the bag or container and/or the fluid content of the container, such as external stiffeners, may also be comprised of non-medical grade printable material, i.e. a material which is not medical grade according to the relevant standard(s), for example not suited for sterilization.

In other words, the functional element and/or the base material and/or a printable material used to produce and/or print the functional element and/or the base material comprises any one or more of the above materials. The materials may be substantially homogeneously, blended or used in different and/or separate parts of the functional element and/or the base material.

The said materials are particularly useful as printable materials. Particularly, thermoplastic materials are useful as printable materials. A particular advantage is provided as the materials can be sterilized which is important when being used as an element and/or compound of a SU bag, particularly a bioreactor. Hence, the risk of contamination may be reduced which is important, as the filling material, for example a biologic material, may be very sensitive to contamination.

Printable materials may even comprise metals, particularly metal powder or granulated metal if the 3D printing comprises a melting of the metal.

Preferably, a single-use container, a SU bag, a functional element, a base material and/or one or more components thereof may be sterilized and/or are sterilized, such that a potential contamination of a potential content of the single-use container may be avoided.

Preferably, the three dimensional (3D) printing technique comprises a fused filament fabrication (FFF), a drop-by-drop application of the printable material and/or a layer-by-layer application of the printable material and/or a fused deposition modelling method (FDM).

A 3D printing process may particularly comprise the so-called fused filament fabrication (FFF) which uses an essentially continuous filament, preferably of a thermoplastic material and/or a fused deposition modelling method (FDM). The filament may be fed from a coil or roll, via a moving and heated printer head, which may be a printer extruder head. Molten material may be driven and/or forced out of a nozzle of the printer head and is deposited onto the base material and the growing functional element. The printer head may be moved, e.g. under computer control, for defining and realizing a desired printed shape of the functional element. Usually, the printer head moves in terms of two dimensional stacked layers, i.e. moving along directions in two dimensions to deposit one (preferably horizontal) plane (particularly corresponding to the plane of the surface of the base material onto which the functional element is to be 3D printed) at a time, before moving in a direction perpendicular to the two dimensional layer (preferably upwards), to begin a new layer. The speed of the printer extruder head may be controlled, to stop and start deposition of printable material and to form an interrupted plane without stringing or dribbling between sections.

A drop-by-drop application of the printable material and/or a layer-by-layer application of the printable material are techniques used in three dimensional printing being particularly efficient and simple.

Preferably, the three dimensional (3D) printing technique comprises printing from a nanoparticle ink and/or spraying atomised metal and/or melting a metal powder and/or aerosol jetting an electronic component.

Particularly, the 3D printing technique may be based on a step of melting a metal powder and printing the same onto the base material. In this case, the metal powder may be considered the printable material. The connection between the base material and the functional element is established by the heating and the functional element may be an electronic component, for example. Alternatively and/or in addition, a metal powder may be implemented in a functional element by heating and melting the powder and printing the same onto the functional element, wherein, at the same time, a connection between the functional element and the melted powder may be established. As an example, a functional element may be composed of a thermoplastic and a layer of gold may be printed onto a surface of the thermoplastic material to provide an electronic connector.

Further, the 3D printing technique may—in addition to printing from a printable material and heating the same— also comprise the printing of electronic elements from metal compositions, such as for example a nanoparticle ink and/or spraying atomised metal and/or aerosol jetting, which may not necessarily require heat supply.

The above feature related to printing from a metal, may allow to easily implement electronic devices, such as electronic connectors, a conductive path, a chip, an RFID antenna or the like at least partially onto and/or into the functional element. This may allow to easily connect a sensor with other electronic elements and/or content or elements of the single-use container. Usually, an implementation of electronic elements may be complicated and may require high effort in production, as multiple steps are required to be performed during the assembly. Including and/or adding the step of printing an electronic device to the step of 3D printing a functional element, hence allows to simplify the production while achieving a high quality of the product. As a result the production costs and the number of production steps may be decreased essentially.

According to another aspect, there is provided a method of producing a single-use container, particularly a flexible or semi-flexible container, based on producing a functional element and connecting the functional element with a base material of the single-use container, particularly a bioreactor, comprising the steps of providing a base material, for example a substantially 2D shaped sheet or a 3D shaped material or a pre-made item such as a pre-made SU bag;

three dimensional printing of the functional element from a printable material on a surface of the base material, such as the outer surface of a bag wall or skin, for example by using a fused filament fabrication (FFF) and/or a droplet-by-droplet and/or layer-by-layer printing method and/or a fused deposition modelling method (FDM); and connecting at least a portion and/or an area and/or a part of the functional element with at least a portion and/or an area and/or a part of the base element by supplying heat to the printable material and/or the base material simultaneously to at least a period or an interval, i.e. a temporal part of the step of three dimensional printing, particularly pre-heating the base element and/or the printable material.

In other words, a base material is provided onto which a functional element is printed. A connection between the functional element and the base material is established, particularly by at least temporarily heating the printable material from which the functional element is produced. In addition, the base material may also be heated. Particularly, when printing a very first layer and/or portion of the functional element onto the base material, the heat may be supplied such that the very first layer and/or portion fuses and/or polymerizes and/or connects with at least a part of the contact area of the base material.

The printing and the heating are preferably performed simultaneously, at least for a certain period of time. The heating causes the base material and the functional element to connect with each other at least partially. The heating may also comprise a pre-heating of a printable material and/or a base material. Pre-heating means heating before the step of three dimensional printing. For example heating the base material on the conveyor belt before or before and during it passes the 3D printer. Another example would be the heating of the printable material inside an extruder prior to or prior to and during the step of printing the functional element.

In other words, the method incorporates a step of three dimensional (3D) printing of a functional element and at least partly connecting the same during the step of printing to a base material, particularly in the production of single-use bags. 3D printing, preferably fused filament fabrication (FFF) and/or a fused deposition modelling method (FDM), may be employed to create or fabricate functional elements having three dimensional features and functional structures, as for example flanges, ports, fill points, sensor holders, sensor parts or the like. This new approach has the advantage of providing a possibility to avoid welding steps to connect separate elements during the procedure of manufacture.

The method further has the advantage of producing a functional element and at least partly connecting the same to a base element simultaneously, thus avoiding separate individual step of manufacture. In other words, a functional element can be printed directly onto a base material, such as a wall element, a (stock) sheet or any other surface which may appear useful.

A further advantage of the method is supported by the fact that no protruding and/or extending surfaces, which are required when separately gluing or welding an element to a surface, are needed, as it is often the case for conventional production techniques (see for example FIG. 1).

As a result, a functional element only requires the space or the area on a surface of the base material, which is limited by its own dimensions, i.e. a surface provided by the shape of the functional element which is used for contacting the base material, without the need for additional areas and/or parts and/or surfaces to establish a contact. Moreover, plenty of functional element can be placed close to each other on the surface of the base material, as no excess area and/or portion is sticking out from the contours of the functional element and the functional elements are only restricted in their distance by their inherent shape.

Preferably, the functional element may be 3D printed onto a surface of either a substantially two dimensional (2D) structure or three dimensional (3D) pre-made bag chamber, respectively, representing the base material. In other words, the base material may be a pre-made bag chamber onto which the functional element may be 3D printed. The pre-made bag chamber may either have a substantially 2D structure or a substantially 3D structure. The substantially 2D structure may be configured to be unfolded into a 3D structure and the 3D structure may be configured to be folded into a 2D structure. It is advantageous to print a functional element onto a folded, essentially 2D structure, however it may also be possible to print a functional element also on an unfolded, essentially 3D structure.

In a preferred embodiment, the step of supplying heat comprises the step of pre-heating the base material, for example on a heated conveyor belt and/or by means of a heat source, such as a lamp and/or a hot air gun.

It is an advantage to heat the base material in view of a reliable polymerization and connection between the materials of the functional element and the base material. Particularly, the heat which is supplied to the base material is provided in addition to the heat provided to melt the printable material.

Preferably, the step of three dimensional printing of the functional element comprises a step of printing from a thermoplastic material and/or at least one of: acrylics (e.g. acrylic resins), EVA, ABS, PC, PE (like HDPE, LDPE, LLDPE), PMMA, PLA, PES, POM, PEEK, PEI, PP, PS, PTFE, TPE.

Other suitable polymer or material may be less preferable but still possible to be applied.

In other words, the printable material, from which the functional element is at least in parts formed, may be any one or more of the above mentioned materials. The said materials may be mixed and/or blended for example as a granulated material before being heated and fused and/or blended and before the 3D printing is performed. Alternatively or additionally, the 3D printing may be performed using different materials at a time such that distinct portions, particularly layers may be composed of different materials.

It is advantageous to print an object from a material which is well-suited as a printable material. Other advantages of using such materials have been mentioned before. The printable material may be provided from stock and may comprise a filament, a granulated and/or fractioned material, a powder and/or a bar. Particularly, the printable material may be a recycled material which may be obtained from removing and/or cutting away excess material from a functional element and/or from a base material. The fused filament fabrication for example usually requires to be fed with a filament of the printable material.

Preferably, the step of three dimensional printing comprises the step of printing from a nanoparticle ink and/or spraying atomized metal and/or a ceramic material and/or melting a metal powder and/or aerosol jetting an electronic component.

In other words, the printable material from which the functional element is at least in parts formed, may also comprise metal compounds, particularly if melting a metal powder is comprised in the method. Metals may be used to produce and/or print electronic components onto or into a functional element. A functional element may be a sensor holder or a sensor port. The functional element may then be provided with an electronic connection for connecting the sensor with other potential electronic devices and/or a grounding.

It is advantageous to print electronic components onto or into a functional element instead of assembling the same either by hand or automatically. A step of assembling electronic components can be very difficult and cumbersome. However, integrating a step of producing electronic components upon printing the functional element, possibly layer-by-layer, is simple and reduces the number of steps as well as the effort. Electronic contacts can also be established reliably by using a printing technique.

Preferably, the method further comprises the step of removing, particularly cutting away a portion of the base material and/or removing, particularly cutting away an excess portion of the functional element.

An excess portion may be a part of the base material which is positioned between a volume essentially enclosed by the base material and a volume essentially enclosed by the functional element. It may be, that a fluid connection should be established between the volume mainly enclosed by the functional element and the volume mainly enclosed by the base material, such as the inside volume of a SU bag. To provide a fluidic connection between the two volumes, the excess portion of the base material may be required to be at least partly removed. An excess portion may also be a part of the surface of the functional element, for example a rough surface that was produced during a coarse layer-by-layer printing. In order to provide a smooth surface, the rough surface may smoothened by taking away a layer thereof.

Preferably, the 3D printing of the functional element comprises a fused filament fabrication, a drop-by-drop and/or a layer-by-layer application.

Standard 3D printing methods may be based on a fused filament fabrication, a drop-by-drop and/or a layer-by-layer application. Such methods have proven simple and reliable approaches for printing a 3D structure.

Preferably, the method further comprises the steps:

removing, particularly cutting away excess material from either the functional element and/or the base material; and at least partly recycling the excess material being removed by particularly reusing the same in the three dimensional printing step and/or in a step of manufacturing the base material, wherein the recycling preferably comprises collecting and grinding the excess material by means of a mill and/or grinder and/or heating the excess material by means of a heating device and/or producing a filament from the excess material by means of an extruder and/or feeding the three dimensional printer with the excess material, particularly with the filament.

A step of recycling unused and/or unneeded and/or waste material is particularly favorable as the amount of material needed and the amount of material wasted can be reduced which is ecofriendly and cost-efficient.

According to another aspect, there is further provided an assembly device for producing a functional element and connecting the functional element with a base material, comprising a three dimensional (3D) printing device for printing a functional element, such as a flange, a handle, a port, a holder, a marker, a fiducial or the like on a surface of the base material, such as the outer surface of the wall and/or skin of a SU bag; and a heating device and/or a heater for supplying heat to the functional element prior to and/or during at least an interval of the three dimensional printing and thereby at least partly connecting the printed functional element to the base material, i.e. establishing a connection at least between parts of the functional element and the base material; and optionally a heating device for pre-heating the base material.

In other words, an assembly device for producing a single-use container or a part thereof, particularly a SU bag and/or at least a part thereof, comprises a base material holder, i.e. means for holding a base material, such as a conveyor belt; a 3D printer for printing a functional element from a printable material onto a surface of a base material, such as an outer surface of a wall of a SU bag; and a heater for at least temporarily heating either the base material and/or the functional element and/or the printable material from which the functional element is printed.

The described assembly device has the advantage of producing a single-use container of materials which are usually challenging to be connected. Further, the assembly device can produce a single-use container with a high surface density of functional elements. The assembly device may be also efficient. A functional element or multiple functional elements may be printed in one single step onto a surface of a base material without the need for cumbersome steps such as gluing, welding, assembling, arranging, or the like. Further, the 3D printer may receive input data defining the design of the item, i.e. the single-use container, particularly the bioreactor and/or the functional elements. A user merely may be required to digitally design the final product, i.e. the single-use container, particularly the bioreactor, particularly the SU bag and/or the functional element on a computer. The data may be transferred to the 3D printer and based on the information the 3D printer can print the desired functional elements. The assembly device can hence produce a high number of single-use containers, particularly bioreactors at a very short time essentially without the need for additional steps being either performed manually or automatically.

Preferably, the assembly device further comprises means for providing and positioning the base material, preferably a conveyor belt, and optionally the assembly device is configured to provide the base material from a roll.

A conveyor belt is useful and efficient for transporting a base material which may be a bulk stock material, i.e. for example a very long sheet being rolled up in a roll. The conveyor belt may pull and/or unfold and/or unroll the base material from the stock pile and/or stock roll in a very efficient and reliable way. The pace of the conveyor belt can be adjusted to the time required at different positions or the production line. Essentially, most or even all production steps, i.e. method steps, may be performed at the conveyor belt.

Preferably, the assembly device comprises means for removing, particularly cutting away excess material from either the functional element and/or the base material, particularly a laser cutter or a conventional cutter; and means for at least partly recycling the excess material being removed, particularly cut off, preferably comprising means for heating the removed material, i.e. the cut away excess material, and means for providing the removed excess material, to the three dimensional printing device and/or to a system which manufactures the base material.

In other words, the assembly device may preferably comprise a recycling system which collects the removed, particularly cut off excess material of the base material and/or the functional element, in a first step. The recycling system may optionally comprise a heater which melts the removed excess material in a subsequent step. Optionally, the recycling system may comprise a system which re-feeds the 3D printer with the recycled and/or collected removed excess material. Optionally, the recycling system may comprise a system, such as an extruder which can produce a new base material from the removed excess material. The single elements of the assembly device may not be dependent from each other and may all be optionally implemented in the assembly device.

The recycling system for recycling the excess material which is removed from either the functional element and/or the base material, being considered the primary base material, may comprise means for heating which is configured to heat the removed excess material. Further, the means for recycling, i.e. the system for recycling the removed excess material, may also comprise the system, for example an extruder, which manufactures the base material at least in parts from the excess material which is removed from either the functional element and/or the primary base material. In an alternative embodiment, the means for recycling the excess material does not comprise a system which manufactures the base material.

In other words, removed sheet bag material and/or removed material of the 3D printed functional element may be recycled into filament stock and fed back into the 3D printer for example as a filament. This may be very efficient and in particular cost-efficient and eco-friendly, as waste can be avoided and less material is needed.

According to the embodiments, it is possible to achieve a reliable and/or an intimate bonding between plastic components and/or between a metal and a plastic component using a 3D printing processes, e.g. Fused Filament Fabrication and/or material jetting. The drop-by-drop or layer-by-layer deposit of the plastic and/or metal above its melting point can heat up the base material, e.g. a plastic bag film and/or other plastic surfaces, sufficiently to melt its very contact surface, without degrading the base material, e.g. a film and to achieve a reliable adhesion.

The described embodiments may particularly benefit in reinforcing bags, providing marks on bags comprising instructions, to corporate a branding or even include warnings in braille. Mounting and location features may be added to hold the bag in place when completed. Inbuilt features or jig points to aid assembly may be printed on to the structure of the bag. Features may be added to aid packaging. Increased material thickness in certain locations may be provided to improve a welding. Sensors or sensor parts may be printed directly (or indirectly) onto bags. The invention may also support reducing the number of parts for fabricating a single-use container as well as reducing effort, particularly the overall time of the fabrication process supporting an efficient process of assembly.

According to another aspect, there is provided a multiple-use container, for example a multiple-use bioreactor, comprising a base material, particularly a wall element and/or a wall and/or skin of the multiple-use container, particularly of a multiple-use bioreactor; and at least one functional element, for example a port, a sensor holder, a sensor part or the like, being at least partially connected with or to the base material, wherein the functional element is obtained by a three dimensional (3D) printing technique from at least one printable material, wherein the printable material is heated during printing thereby (so as to) at least partly connecting the printed functional element to the base material.

It is self-explanatory that all optional embodiments which have been described for a single-use container may be combined—if not contradictory—with a multiple-use container according to the above aspect.

In the following, example embodiments are described in detail. Single features being described in a particular embodiment may be arbitrarily combined, given that they are not excluding each other. In addition, different features which are provided together in the example embodiments are not to be considered restrictive to the invention.

FIG. 1a is a schematic view illustrating conventional technique connecting of a functional element with a base material using welding;

FIG. 1b is a schematic view illustrating a 3D printed functional element connected with a base material according to an example embodiment;

Figures 6A, 6B:
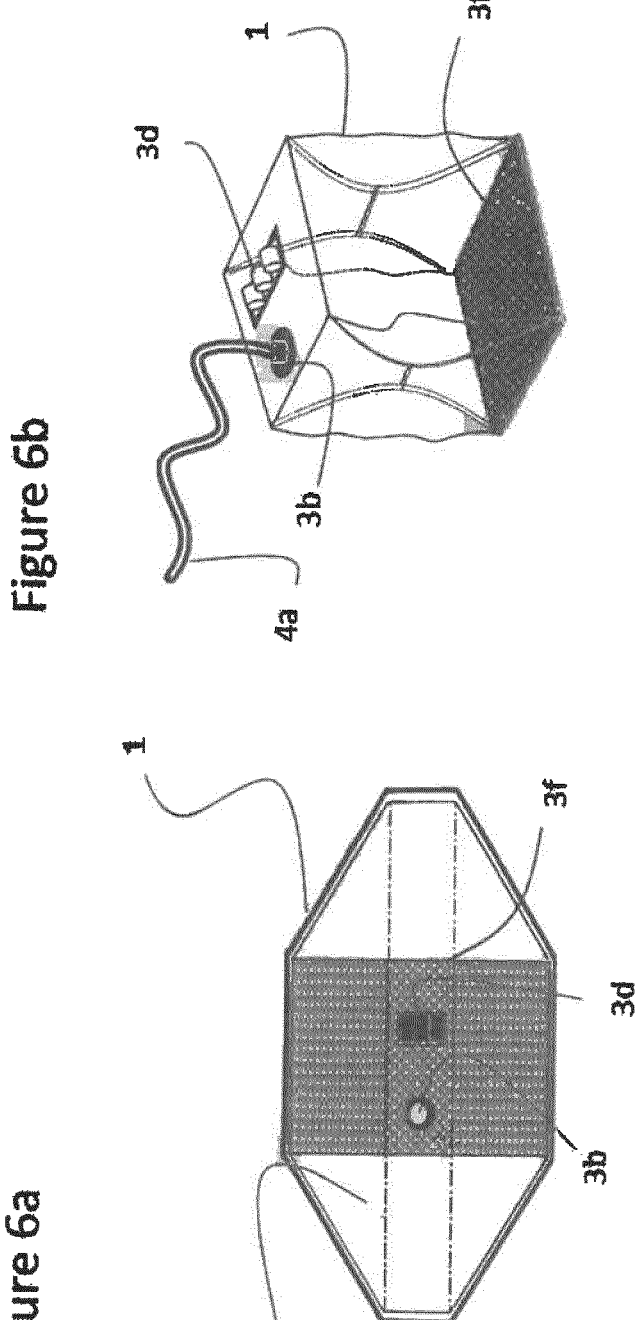

FIG. 6a is a top view of a pre-made single-use container, i.e. a single-use bag with functional elements being folded into a substantially 2D structure according to an example embodiment; and FIG. 6b is a perspective view of the pre-made single-use container, i.e. single-use bag with functional elements being unfolded into a substantially 3D structure according to the example embodiment of FIG. 6a.

In the following, the differences between a conventional production technique and a production technique in terms of the present embodiments is discussed in general. A more detailed comparison is provided subsequently, particularly in view of FIG. 1a and FIG. 1b.

A conventional production technique of single-use container and the like typically comprises a step of welding when elements and/or parts, such as a conventionally produced functional element and a base material, need to be connected to each other. The present embodiments, comprise a step of 3D printing a functional element right onto a base material and connecting them at the same time with each other, particularly substituting for the step of conventional welding.

Usually, in a conventional production procedure, components are produced separately and then welded onto a bag surface in a separate stage. Bag chambers are often made of thin mono or multi layers film of plastic and/or synthetic material(s) (typically from approx. 80 μm to approx. 400 μm). Thermal welding of a plastic component onto a bag film has a strong impact on the component material selection and interface design, to achieve a proper melting between a thin bag film and a more massive component interface.

The main risk is to completely fuse or degrade the film before the colder component interface has reached the appropriate melting point. Advantageously, a drop-by-drop or layer-by-layer application of the plastic molding compound above its melting point, as it can be the case for a 3D printing technique, can heat up the plastic bag film, i.e. a base material, sufficiently to melt its contact surface, without degrading the film and to achieve a good adhesion between plastic component and film. Consequently, the scope of the embodiments described herein may allow to enlarge the number of possible component materials and design options to better fit to the component targeted function, i.e. the function of a functional element.

Further, materials may be used and/or processed, by means of the embodiments described herein, which are usually difficult or even impossible to be used and/or processed in such steps which require the welding of assemblies. Such materials comprise for example HDPE components (which may be functional elements) being connected to EVA and/or LLDPE film layers (which may be base materials); ABS and/or PC components (which may be functional elements) being connected to PE film layers (which may be base materials). In other words, the said material combinations may be realized using the method, including 3D printing, according to the present embodiments. However, the conventional techniques, particularly comprising a step of welding the components, may hardly or not at all allow to combine the said materials.

The welding process of a plastic component, e.g. a functional element, onto SU bag films, e.g. a base material, requires the application of a pressure onto the assembly to achieve a reliable contact at the film-component interface during heating, i.e. the time during which the heat is supplied. This can potentially have an impact on the film thickness and/or the resistance of the welded assembly. The 3D printing process according to the present embodiments can however provide a more gentle and reliable technique, as no pressure is applied on the melted interface.

For making the process of welding possible, the plastic component, i.e. the functional element, is required to be designed with a quite large extension, i.e. the elongated portion, to allow access of the welding tool, i.e. the welding machine. The embodiments described herein essentially allow to design more compact components, while still having the appropriate adhesion surface to reach the target resistance. Potential associated benefits comprise: reduction of bag weight, possibility to position more functional elements and functionalities on a small SU bag surface, locate functional components closer to the edges of the SU bag if required.

The position, configuration and the number of functional elements and components on a SU bag typically depends on the dimensions of the welding machines and the designs of the welding components, particularly the functional elements. A final SU bag assembly is therefore designed taking into account a set of defined components, i.e. functional elements. The welding parameters and the location on a bag, at which functional elements may be applied usually need to be pre-validated. In this respect, the embodiments described herein may also allow a higher degree in flexibility, particularly in terms of customization of a SU bag and late and/or spontaneous and/or individual differentiation of standard bag chambers. Such a "late" and/or spontaneous differentiation of bag chambers may be possible if a functional element is 3D printed on a bag chamber, not only on a film roll. The term "late" may refer to a late stage, at which a SU bag has been produced already, while functional elements are still to be applied and/or connected to the SU bag. Furthermore, the 3D printing opens up significantly expanded design possibilities for the component as for instance compared to injection molding techniques.

3D printing a plastic part, such as a functional element, directly onto a base material, such as a SU bag film, may also allow to bond plastic parts on the base material and/or SU bag surface that would necessitate a very specific and difficult welding process as well as a customized welding tool, because really large, or even massive components, such as functional elements, need to be processed and/or connected. Further, a component which should be located and/or connected in SU bag areas which are not accessible by a welding tool may also limit the conventional production. For example, if such a component should be positioned on an external bag surface which does not comprise a hole and/or an opening in the film, difficulties to position a welding tool inside of a pre-made bag chamber may occur. Some examples for (new) applications which may be realized with some of the embodiments described herein are given in the following: strong stiffeners, holders for tubes and components, features to locate the bag into the hard container.

In general, most SU bags need to carry information during their life cycle, such as bag volume, product description, branding info, logo, batch number and the like. In some cases, the external layer material of the SU bag and the surface treatment allow printing such information directly onto the SU bag. Otherwise a label, such as a plastic layer is applied to the surface of the SU bag. The label as well as the information can be printed onto the SU bag's surface using the 3D printing technique according to the embodiments described herein. Conventional methods can however be critical in view of the risk of ink migration and/or damage of the SU bag caused by the label adhesive, as well as contamination of the SU bag's content with label adhesives through the bag film and possible unwanted chemical reaction and/or interaction with the content contained in the bag. Hence, the embodiments described herein are also useful for printing an information and/or a label with or without an information onto the SU bag film or other plastic components with a characterized material, particularly being validated for biocompatibility with bioprocess fluids.

In addition or alternatively, a layer or multiple layers of metal may be applied onto a plastic component, such as a functional element and/or a base material without the need for conventional techniques, such as gluing, welding, soldering or the like. Conventionally, it is possible to insert metallic parts into plastic injection moulds to trap the metal part into the plastic. The deposition of thin metal layers on a plastic part is also possible by using metal coating. However, this requires a component to be immersed into a chemical bath, to be sputtered and/or treated by metal evaporation. In this respect, the embodiments described herein may allow to bond electronic components, particularly thin electronic paths to plastic components, such as a functional element and/or a base material, and/or to encapsulate a small sensor on a SU bag surface (inside or outside of the bag) or on plastic components, such as a functional element.

In the following, a concrete example of a conventional (welding) production technique together the according product of this technique is discussed in view of FIG. 1a and compared to an technique comprising a step of 3D printing a functional element 3 onto a base material 2 according to an example embodiment.

Figures 1A, 1B:
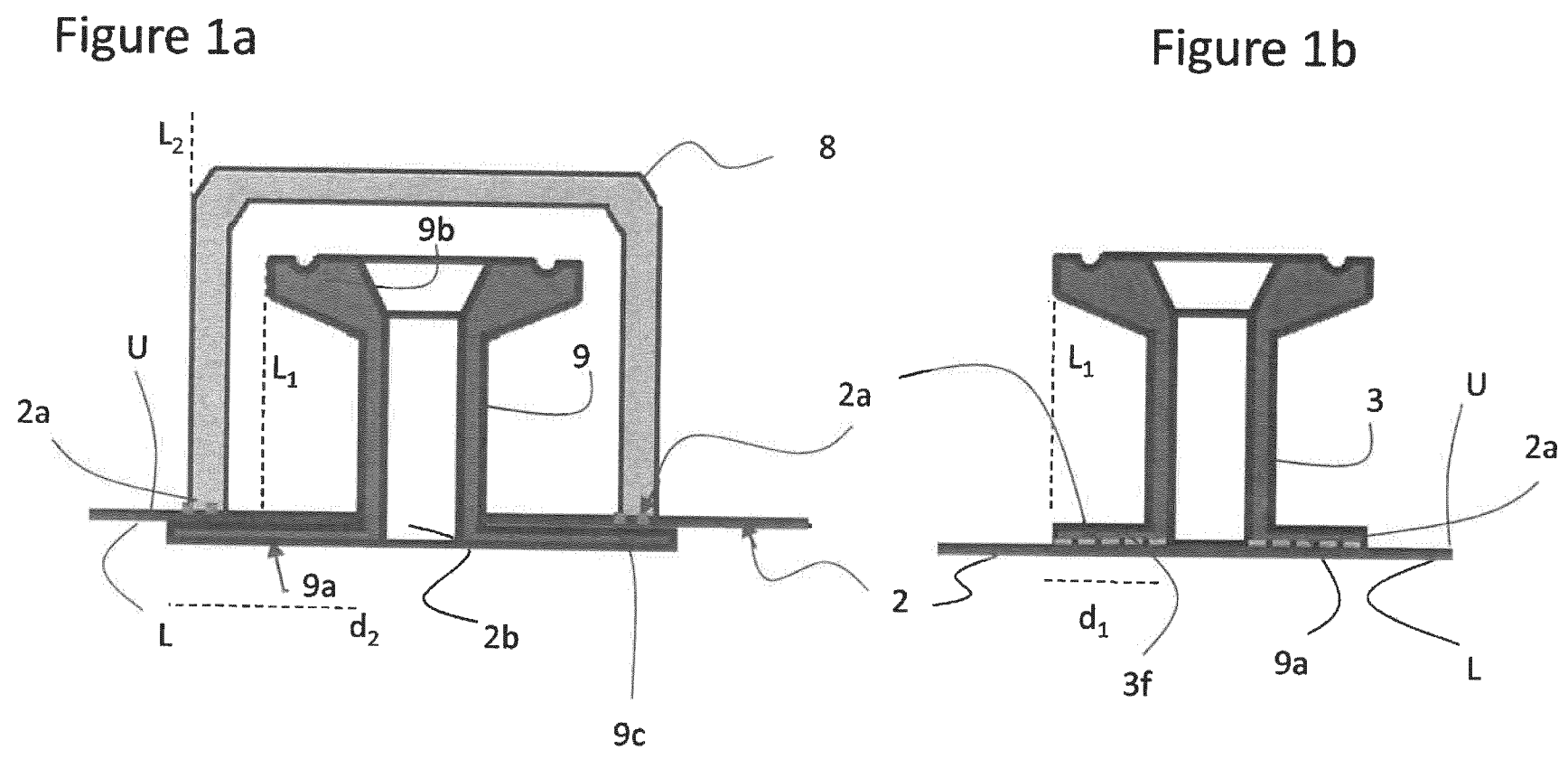

FIG. 1a is a schematic view illustrating an example of a conventional production step. The production comprises a step of connecting a functional element 9 with—and/or to a base material 2 using a step of welding. The conventionally produced functional element 9 has been fabricated in a separate step before the step of connecting the parts to each other. Possibly, the conventional functional element 9 has even been purchased from a producer. For connecting the conventional functional element 9 with and/or to a base material 2, the conventional functional element 9 comprises an elongated portion 9a with an excess surface 9c protruding from the main body 9b of the conventional functional element 9. The elongated portion 9a is required for providing a surface, i.e. substantially the excess surface 9c for the step of welding the parts together. The elongated portion 9a may also be called an assembly flange (not to be confused with a flange as defined herein for connecting parts such as tubes or a tube with a container, for example).

The elongated portion 9a extends over the dimensions of the main body 9b of the conventional functional element 9, as a welding machine 8 is required to be put over the main body 9b of the conventional functional element 9 to reach the elongated portion 9a, such that the step of welding can be performed at or near the excess surface, particularly at the contact surface 2a, where the welding machine 8 contacts the base material 2.

The base material 2 comprises an opening 2b through which the main body 9b of the conventional functional element 9 can be pushed or pulled or driven, such that the elongated portion 9a is positioned at least in parts on one side of the base material 2 facing one surface, i.e. the lower surface L of the base material 2 in the drawing. The main body 9b of the conventional functional element 9 is at least in parts positioned on the opposite side of the lower surface L of the base material 2, extending from the upper surface U of the base material 2.

A welding machine 8 is put over the main body 9b of the conventional functional element 9 and contacts at least in parts the upper surface U of the base material 2. At the surface 2a, the connection is established by the welding machine 8. The welding machine 8 is configured to provide heat to the below material, i.e. the surface 2a being part of the upper surface U of the base material 2. The heat migrates through the base material along its layer thickness and into the upper surface of the elongated portion 9a of the conventional functional element 9, such that the fusion and/or connection can be established. Particularly, a fusion based on a polymerization and/or a polymeric reaction allows the parts to connect.

The step of welding comprises several steps, as illustrated. An opening 2b in the base material 2 is required and needs to be made before the connecting. The arrangement of the conventional functional element 9 with respect to the base material 2 and the opening 2b is also required before the step of connecting and after the opening 2b has been made. The welding machine 8 needs to be positioned, particularly put over the conventional functional element 9. Only, when the said steps have been performed, the step of welding can be carried out. In addition, it may be required to provide and/or adjust the welding machines 8 to the shapes of different conventional functional elements 9.

FIG. 1b is a schematic view illustrating an example 3D printed functional element connected with a base material according to the present disclosure. The functional element 3 comprises a reinforcement structure 3f which is connected with the base material 2 at the surface and/or interface 2a. The main body of the functional element 3 is printed on top of the reinforcement structure 3f.

Alternatively, it may also be possible to print the functional element 3 directly onto the base material 2 without providing a reinforcement structure 3f. It can be seen from comparing the drawings of FIG. 1a and FIG. 1b that the elongated portion 9a of the conventional functional element

9 is longer than the reinforcement structure 3*f*. In addition, the reinforcement structure 3*f* may be realized even shorter and much thinner than an elongated portion 9*a* of a conventional functional element 9. The 3D printed functional element 3 may even be realized without any reinforcement structure 3*f*.

The lines $L_1$ in FIG. 1*a* and FIG. 1*b* indicate the shadow, i.e. the orthogonal projection of the shape of the functional element 3 onto the below plane, i.e. in the present figures basically the plane of the base material 2. The elongated portion 9*a*, i.e. the assembly flange, needed in the conventional technique when applying a step of welding (FIG. 1*a*), extends over the projection line $L_1$. The elongated portion 9*a* is longer to allow the welding machine 8 to apply pressure and heat along the line $L_2$, indicating the shadow, i.e. the projection of the shape of the welding machine 8 onto the below plane, i.e. in the present figures basically the plane of the base material 2. In other words, the length $d_2$ of the elongated portion 9*a* is required to exceed the line $L_1$ in order to be long enough to allow the welding machine 8 to apply pressure and heat to its surface 9*c*. The length $d_2$ depends on the structure of the functional element 3. If the functional element 3 has a large structure in terms of the projection/shadow onto the plane of the base material, the elongated portion 9*a* is also required to be large. The length $d_1$ of the elongated portion 9*a* according to the example shown in FIG. 1*b* can be shorter as compared to the length $d_2$ required in the conventional (welding) technique. The length $d_1$ of the elongated portion 9*a* according to the example shown in FIG. 1*b* may particularly be short such that it does not exceed/cross the line $L_1$. The elongated portion 9*a* provides a surface for contacting the base material 2 with the functional element 3. Accordingly, this surface can be reduced according to the example shown in FIG. 1*b*, since the functional element 3 is printed directly onto the base material 2. Particularly, the elongated portion 9*a* is welded over its substantially entire surface to the base material 2.

In the following, example of a preferred SU bag 1 with functional elements 3 is discussed.

Figure 2:
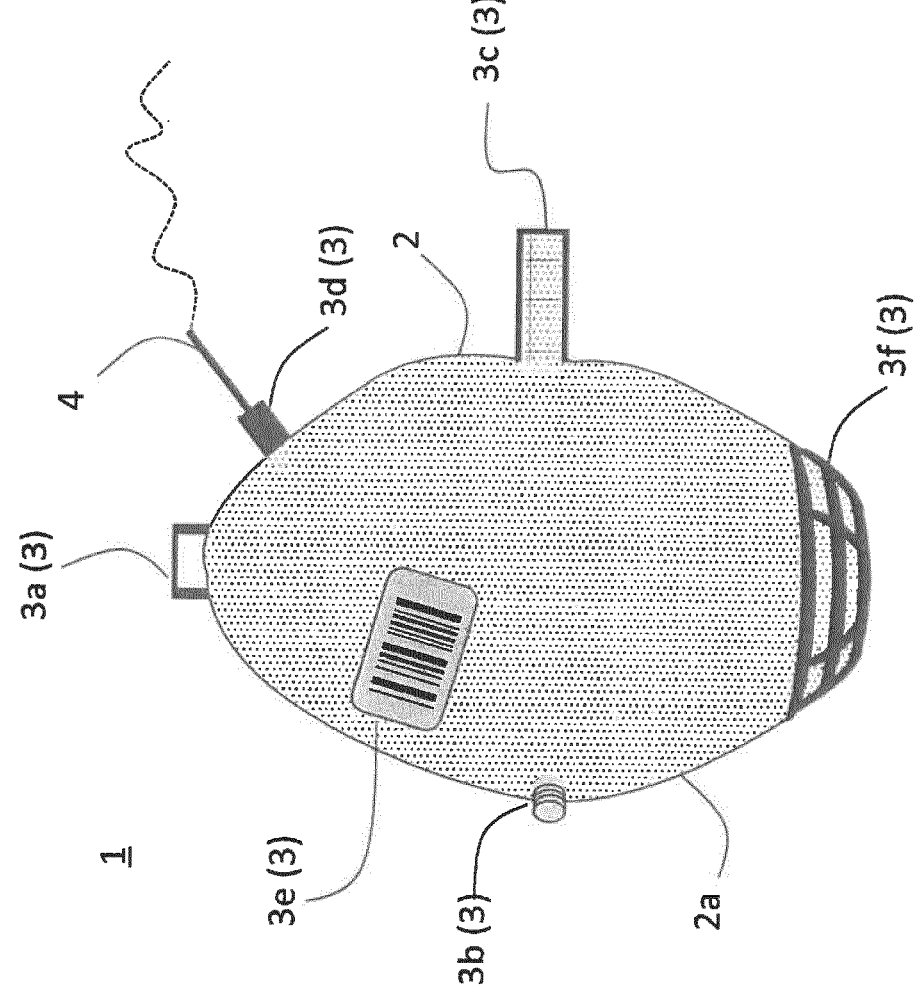
FIG. 2 is a schematic side view of a single-use bioreactor, i.e. a single-use bag, according to an example embodiment.

FIG. 2 is a schematic view of a bioreactor, i.e. essentially a single-use (SU) bag 1 according to an example embodiment. The SU bag 1 comprises one or more functional elements 3 which have been 3D printed onto the base material 2 being a precursor of a SU bag 1 or onto the outer surface 2*a* of the SU bag wall or skin, wherein the SU bag may be a pre-made product. In general, the base material 2 is a composite material of the SU bag 1 onto which a functional element 3 is printed. Alternatively, the functional element 3 can also be printed onto a pre-made SU bag. The base material 2, i.e. the precursor of a SU bag, has a surface 2*a*, being also the surface 2*a* of the SU bag 1. The functional elements 3 are printed onto the surface 2*a*. In the present drawing, this surface 2*a* is represented by the outer side surface of the wall and/or skin of the SU bag 1.

The SU bag 1 comprises a handle 3*a* which may be used for holding, lifting, hanging and/or carrying the SU bag 1. The SU bag 1 further comprises a functional element 3 which is either a junction 3*b* and/or a flange and/or a port for establishing a fluid connection between a tube and the inside volume of the SU bag 1. The junction 3*b* may be threaded to provide a secure connection between a tube and the SU bag 1. Alternatively, other connection types may be provided, for example comprising a plug and/or a bracket or the like.

Moreover, the SU bag 1 comprises a port 3*c* which may for example be an optical port comprising a window, not being shown in the present drawing. An optical measurement, such as a spectroscopic measurement may be performed through the window. The port 3*c* may for example be configured to at least partially host an optical sensor. The port 3*c* may be 3D printed only in parts, as for example the windows may be arranged after the 3D printing of the port 3*c* has been completed. Typically, glass or other materials which are used as optical windows do not qualify as printable materials and therefore it may be required to assembly the windows, separately. A frame for hosting a window may be printed as a functional element 3. However, polymeric window materials may also be printed during the step of 3D printing the port 3*c*. As an alternative or in addition, the port 3*c* may also comprise an opening for establishing an access to the inside of the SU bag 1, which is however not explicitly shown in the present figure.

The bioreactor 1, i.e. essentially a SU bag according to the present example embodiment of FIG. 2, comprises a sensor holder 3*d* with a sensor 4. Alternatively, the sensor holder 3*d* may also be a tube holder. A sensor holder 3*d* may also be combined with a reinforcement structure, which is not shown in the present drawing. For example, a reinforcement or supporting structure may be printed onto the SU bag wall. The sensor holder 3*d* may be printed at least in parts onto the reinforcement structure.

The sensor holder 3*d* may also be provided with electronic components, not being shown in the present drawing. The electronic components may be implemented, particularly printed upon 3D printing the sensor holder 3*d*.

According to the drawing of FIG. 2, the sensor holder 3*d* at least partially hosts a sensor 4 which may be in contact with the medium inside the SU bag 1. In this case, the sensor holder 3*d* preferably provides a physical access to the inside volume of the SU bag 1. Alternatively, the sensor 4 is not required to be in contact with any medium within the inside volume of the SU bag 1. For example, the sensor 4 may be a temperature sensor which merely probes the temperature at the outer surface 2*a* of the wall of the SU bag 1.

The SU bag 1 further comprises a label 3*e*, i.e. a field and/or a layer of material being 3D printed onto the outer surface of the wall of the SU bag. In the present drawing, a bar code is printed onto the label as well. Alternatively or in addition, a label may be comprise an RFID code having an antenna element (not shown in the present drawing). Further, a label may contain other types of information, possibly indicating the content inside the SU bag 1.

The present bioreactor, i.e. essentially the SU bag 1 of FIG. 2 also comprises at least one functional element 3 which is a structure 3*f*, i.e. a stabilizing and/or stiffening and/or reinforcement element 3*f* which e.g. allows the SU bag 1 to stand upright. The reinforcement element 3*f* has a shape of a basket in the present case and is basically comprised of a filament structure having ribs, e.g. a thick and/strong filament rib structure in the form of a basket.

It is self-evident, that such a reinforcement element 3*f* may be applied along edges or in areas, where the wall of the SU bag 1 requires support for avoiding damages for example, such as at the bottom of a SU bag 1. A ribbed reinforcement element 3*f* may for example also be essentially applied all over the surface 2*a* of the wall or skin of the SU bag 1 to provide particularly strong stability and support.

Preferably, the functional elements 3, such as the handle 3*a*, the junction 3*b* and the sensor holder 3*d* are provided with a reinforcement structure, which is not explicitly shown in the present figure. The reinforcement structure may be a 3D printed layer which is printed onto the base material 2 upon printing the functional element 3 in order to locally stiffen and support the stability of the base material 2. The reinforcement structure may surround the contacting area between the functional element, such as the handle 3*a*, the junction 3*b* and the sensor holder 3*d*, and the base material to stiffen the elements and to avoid that the connection between the functional element 3 and the base material 2 ruptures and/or degrades easily.

Figure 3:
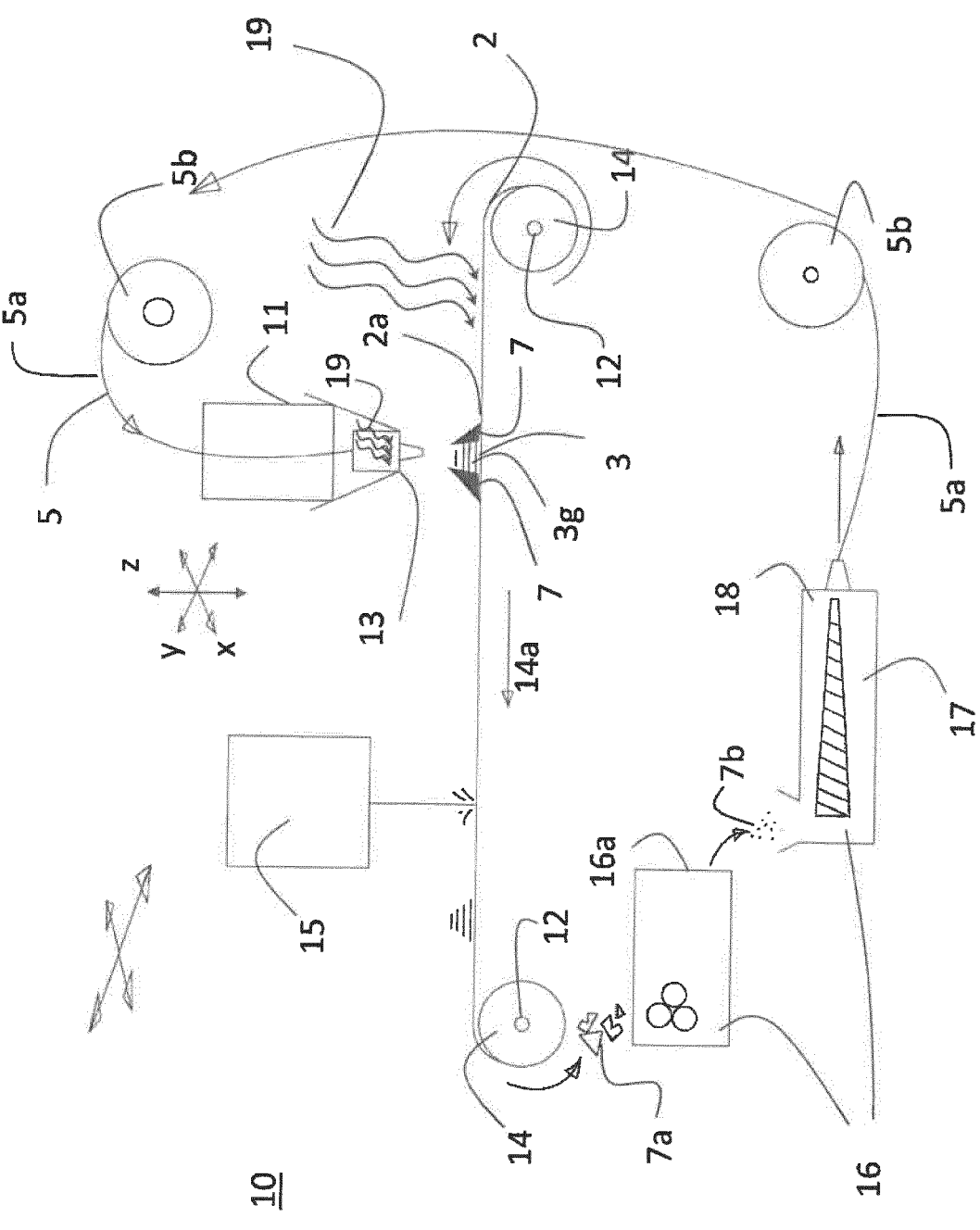
FIG. 3 is a schematic view of an assembly device according to an example embodiment.

FIG. 3 is a schematic view onto an example assembly device 10 for producing SU bags 1 or parts thereof. The assembly device 10 is provided with means 12 for providing and positioning a base material 2, i.e. a conveyor belt in the present case. A roll 14 of base material 2 is unrolled by the conveyor belt 12 into the direction 14*a*.

An example production line is illustrated in the present drawing. A 3D printing device 11, particularly comprising a printer head, which may be a printer extruder head, is positioned above the surface 2*a* of the base material 2 onto which a functional element 3 is to be printed. The printer head comprises a heater 13 for substantially melting the printable material. The 3D printing device 11, particularly the printer (extruder) head scans a layer in the x-y dimension indicated by arrows in the drawing. In other words, the printer head of the 3D printing device 11 scans a horizontal plane (in the x-y dimension) while printing a substantially two dimensional layer or sheet 3*g*, i.e. a very thin layer, of printable material 5 onto the surface 2*a* or onto an already printed layer 3*g* or a stack of layers 3*g*. By heating the printable material 5 the material can be deposited on the surface 2*a* of the base material 2 thereby partially melting the base material 2 to fixedly secure the printable material 5 to the base material 2, particularly to fuse the printable material 5 and the base material 2 to unite or blend them into a whole, as if by melting together. In other words, by 3D printing the printable material 5 directly onto the surface 2*a* of the base material 2 no separate melting step is necessary, so that an efficient connection of the functional element 3 to be created and the base material 2, particularly allowing for a small footprint (see e.g. FIG. 1*b*) as compared to a conventional welding (see e.g. FIG. 1*a*), is possible. In this connection it is conceivable that the base material 2 may be additionally heated (e.g. by a unillustrated heater) so as to allow an improved mechanical connection of the functional element 2 being printed with the base material 2. As a result of the above, the printable material 5 is heated during the three dimensional printing so as to at least partly connect or mechanically secure the printed functional element 3 to (the surface 2*a* of) the base material 2 particularly in a sealed or fluid-tight manner.

Once, the layer 3*g* has been completed, the printer head of the 3D printing device 11 moves into a different position substantially in a perpendicular direction of the x-y plane. As the x-y-plane is substantially a horizontal plane, the perpendicular direction is a vertical direction, indicated by the arrow and the sign "z".

Again, the printer head of the 3D printing device 11 scans the horizontal plane (in the x-y dimension) while printing a further substantially two dimensional layer or sheet 3*g* onto the previous layer 3*g*. The described steps are or may be repeated until the functional element 3 has been completed. The instructions of how the functional element 3 may look like and how the according method steps are to be performed may be computer controlled, particularly may be provided from a software program running on a computer to which the 3D printer 11 may be connected.

Preferably, the 3D printing is performed using fused filament fabrication (FFF) and/or a fused deposition modelling method (FDM) and/or layer-by-layer application and/ or droplet-by-droplet application. The 3D printing device 11 is fed with a filament 5*a* of printable material 5 (such as a metal or thermoplastic filament) being provided from a roll 5*b*. Alternatively, the printable material 5 may be fractioned and/or grinded and/or fragmented material, such as a powder or a granule. The printable material 5 particularly may be chosen such that a functional element 3 formed thereof by 3D printing may be pre-sterilized together the base material 2 (e.g. formed into the SU bioreactor 1) particularly by a sterilization process such as gamma irradiation or steam sterilization.

In other words, the 3D printing device 11 may print (e.g. using the fused filament fabrication, FFF, technique and/or a fused deposition modelling method (FDM)) the functional element 3 in a layer-by-layer and/or in a droplet-by-droplet technique directly onto the surface 2*a* of the base material 2 thereby mechanically securing the functional element 3 to the base material 2. In such a way a fluid-tight or sealed connection between the functional element 3 and the base material 2 is advantageously possible. Heat 19 is supplied, for example by the heat supplier 18, particularly a heat supplier of an extruder head, in order to fuse and/or connect and/or melt the printable material 5 for the functional element 3 being printed with the material of the base material 2 and with the layers 3*g* which may have been printed already. Typically, a first printed layer 3*g* contacting the surface 2*a* is at least partially connected to the surface 2*a* of the base material 2, whereas the further following layers 3*g* are connected at least in parts to the layers 3*g* which have been printed, already.

Heat 19 may also be supplied to the base material 2 by a heat supplying means (not shown), which may for example be or comprise any one or more of a heated conveyor belt, hot air, an infrared radiation source and the like. Heat 19 might be applied to the top (as shown) or to the bottom of the base material. In other words, the base material 2 may be permanently heated during the entire process or pre-heated before and/or while the step of 3D printing is performed.

Care is taken by adjusting the temperature. To this extent it is advantageous to reach the melting points of the two materials to bond just at the interface, before the one or more layers of the back sheet material are completely melted. The temperature depends e.g. on the base sheet formulation, base sheet thickness, targeted cycle time, and component material formulation and thickness.

Typically, the 3D printing device 11 may be (particularly computer-controlled) controlled so as to be moved in three dimensions (for example xyz dimension) to realize the structures of the functional element(s) 3. The 3D printing device 11 may therefore be guided or controlled by a computer (e.g. based on a digital program or software) based on the data or design input from a designer. Therefore, a user, being the designer, may virtually and/or digitally construct and/or design the structure of the functional element(s) 3 and/or the SU bag 1. The data being generated therefrom may be transferred to the 3D printer 11, which follows the computer instructions and realizes the functional element(s) 3.

As an alternative or in addition, (not shown in the present drawing) the means 14 for providing and positioning the base material 2, particularly a stage and/or a conveyor belt, may be configured to move in three dimensions. In this case, the 3D printer 11 is not necessarily required to move during the process of printing, while the stage follows the instructions provided by the computer such that the layer from the 3D printing device 11 is applied to the right positions of the base material 2.

The functional element 3 comprises parts and/or portions which refer to excess material 7. Such excess material 7 is considered to be removed in a later step. The 3D printing device 11 may be fed with a printable material 5, for example a filament, granulate, a powder, a fractionated material or the like. The printable material 5 may also comprise at least in parts excess material 7a, 7b or derivatives thereof.

The next step in the example production line according to the present example assembly device 10 is a step of cutting off excess material 7 of the functional element 3 after (at least part of) the printing has been completed. Therefore, the assembly device 10 comprises means 15 for removing, particularly cutting off excess material 7, which may preferably comprise a laser cutter. In the illustrated example, merely excess material 7 from the functional element 3 is removed, however, also excess material from the base material 2 may be removed.

In a subsequent step of the example production line of FIG. 3, the excess material 7a which has been removed, is collected by means 16 for recycling the excess material 7a, i.e. a system for recycling removed material 7a. A mill and/or grinder 16a is provided which grinds and/or pulverizes the fragmented removed excess material 7a. The pulverized excess material 7b is transferred into a system 17 which provides the removed material 7b to the 3D printer 11. The system 17 may comprise an extruder with a heater 18 which is configured to extrude a filament 5a out of the removed material 7b. Accordingly, the filament 5a can be produced and rolled up into a filament roll 5b. The filament roll 5b may be used to feed the 3D printer 11 with a filament 5a of a printable material 5 for performing 3D printing using the fused filament fabrication (FFF) and/or a fused deposition modelling method (FDM).

Optionally, the system may (alternatively or in addition) be configured to manufacture new base material 2 from the excess material 7a, 7b, such as a sheet (not shown). The system 16 for recycling removed material 7a may therefore also comprise means for heating which is configured to melt the pulverized removed material 7a, 7b. The system 16 for recycling removed material 7a, 7b is advantageous, as waste can be avoided and the amount of material needed for the production can be reduced.

Figure 4:
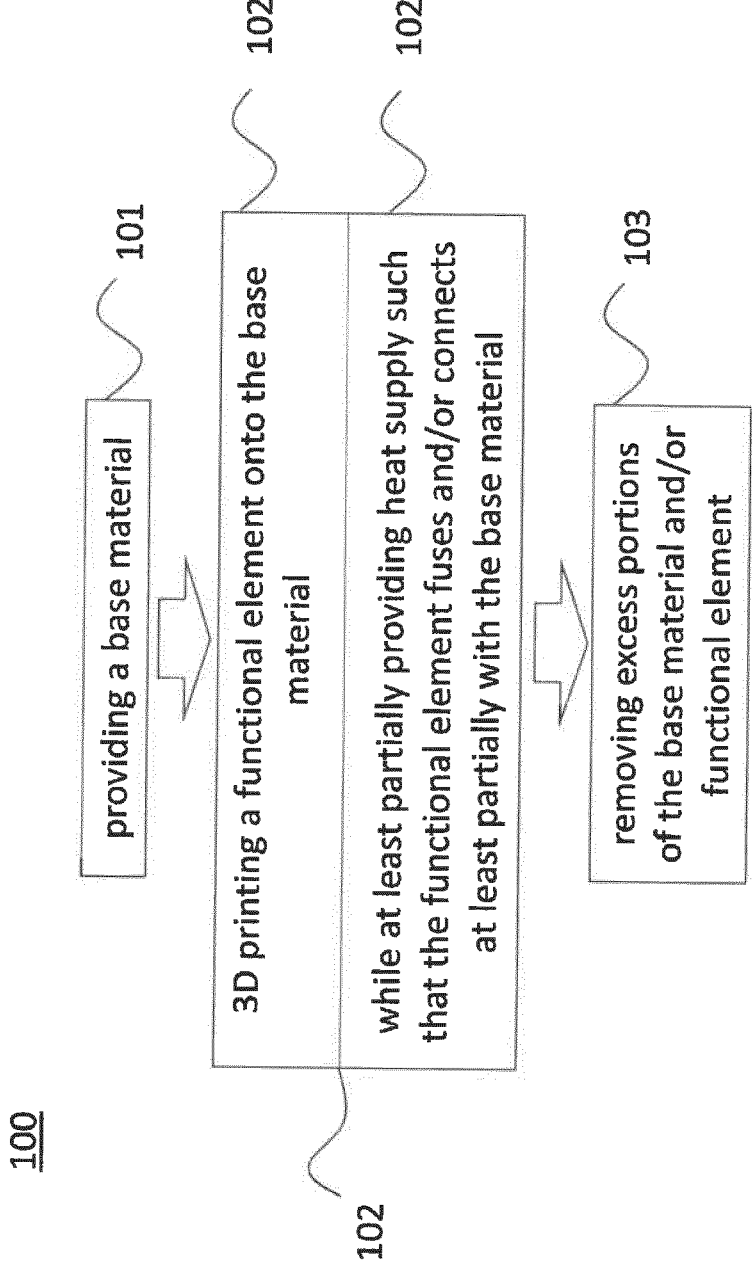
FIG. 4 is a flow diagram illustrating the steps of a method for producing a single-use container according to an example embodiment.

Essentially, the method steps, being performed in the production line presented together with the assembly device 10 of FIG. 3, are schematically summarized in FIG. 4. The method 100 comprises the step of providing 101 a base material 2, such as a sheet and/or a substrate and/or a pre-made bag and/or a bag wall and/or a bag skin.

The step of 3D printing 102 the functional element 3 onto a surface of the base material 2 is separated into two steps which may be at least partly occurring at the same time (i.e. be not temporarily divided). Particularly, the separation is merely for illustrating two different actions being taken during the 3D printing step 102. In step 102a, the 3D printing of the functional element 3 onto the base material 2 is addressed. In step 102b, the supply of heat 19 to either the functional element 3 and/or the base material 2 for establishing a connection and/or fusion between them is addressed. In one particular case, the heat 19 is already supplied upon the 3D printing, as the printable material 5 is heated and melted and therefore hot enough to fuse with the base material 2 as it first contacts its surface 2a. In other examples, the heat 19 may be (at least partly) supplied as a separate action which is taken, e.g. by means of a separate heater (not shown).

In summary, a two dimensional sheet which may be a single layer or a multiple layer base material 2, may be loaded directly and/or fed in correspondence to (e.g. under) the at least one printing head or a 3D printing device 11, particularly held firmly in position in an optimal environment. The printer head may approach (e.g. descend to) the surface of a base material 2, such as a 2D material and/or a pre-made SU bag and/or a sheet and/or a portion of a SU bag film, and deposit a printable material 5 onto the upper surface 2a of the sheet 2 thereby forming a bond between or fusing the two substances and producing the functional element 3 after all being mechanically fixed to the base material 2. This process may iteratively continue layer by layer to construct a 3D form of the functional element 3.

Once the completed features and/or structures and/or shapes (i.e. the one or more functional elements 3) are added to the surface 2a of the base material 2, the sheet, i.e. the base material 2 having the functional element 3, may be further conveyed along to a second stage where one or more fiducial marks, indicating cutting lines, may be read and/or at least one pattern of the SU bag section(s) may be cut.

When the one or more parts are cut, they may be removed from the conveyor belt and welded into a SU bag. At this stage, it may be possible for waste and/or removed excess material 7a to be fed into a grinding stage, i.e. a mill 16a or a grinder, being pelletized and moved on to an extruder and/or a system 17 which particularly provides the removed material 7a to the 3D printer 11, particularly being in the form of a filament 5a. The system 17 may comprise an extruder. Specifically, the removed, particularly cut off excess material 7a may be extruded as a filament 5a and either be used for other applications and/or to feed the 3D printer 11 at the beginning of this process and/or to fabricate a new base material 2.

An alternative or additional option is to position a 2D or 3D pre-made SU bag chamber, representing the base material 2 in correspondence to (e.g. right under) the at least one printing head of the 3D printing device 11. In case a pre-heating of the SU bag surface may be advantageous, this may be performed particularly by heat convection with pulsed hot filtered air and/or infrared radiation before 3D printing the functional element 3.

It should be understood that the 3D printing technique disclosed herein is explicitly not restricted to a SU bag 1 or to the functional element 3 as described herein. Any plastic element may be connected to a base material using the technique according to the embodiments described herein.

The example method 100 of the scheme illustrated in FIG. 4, also comprises a step 103 of taking off and/or removing and/or cutting off or cutting away excess material 7 from the base material 2 and/or the functional element 3. The removed, particularly cut off excess material 7a may be processed in a subsequent optional step (not shown in the present drawing) by means of a recycling system 16 according to the example shown in FIG. 3.

Figure 5:
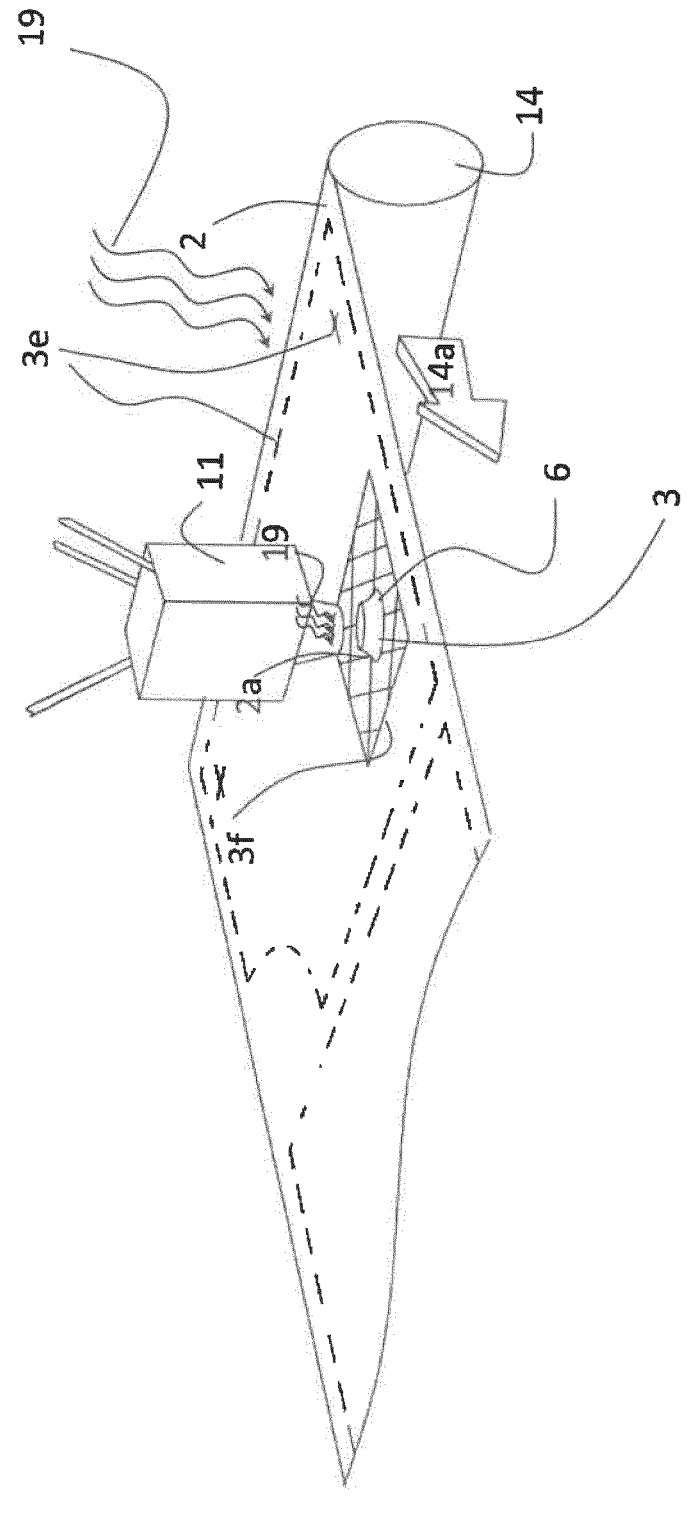
FIG. 5 is a perspective schematic view of a 3D printer printing a functional element onto a base material according to an example embodiment.

FIG. 5 is a detailed view of a printing device 11 during the step of 3D printing a functional element 3 onto a surface 2a of a base material 2. The base material 2 is provided from a stock roll 14 which is unrolled into the direction 14a for the step of 3D printing. The 3D printer 11 particularly has printed one or more markers 3e (such as fiducial marks) e.g. for guiding a cutter which is required to cut along a guiding line. The 3D printer has also printed a reinforcement structure 3f being in direct contact with the surface 2a of the base material 2. The drawing illustrates the moment when the 3D printer 11 is about to print a functional element 3 onto the reinforcement structure 3f. The functional element 3 which is printed onto the reinforcement structure 3f may not be in direct contact with the surface 2a of the base material 2.

The combination of the reinforcement structure 3f and the functional element 3 may be considered one single functional element, wherein the portion which is in contact with the surface 2a of the base material 2 is essentially the reinforcement structure 3f. Alternatively, however less intuitive, the reinforcement structure 3f may be considered a base material 2 instead, onto which the functional element 3 is 3D printed.

The advantage of providing a reinforcement structure 3f between a base material 2 and a functional element 3 is an improved stability and resistance. The risk of damaging the base material 2 upon bending the functional element 3 is reduced as a reinforcement structure 3f is provided in between the two parts. A force which is applied to a functional element 3 can be distributed over a larger area in this particular case. A rupture of the seam or the connection area between functional element 3 and base material 2 can hence be avoided. The reinforcement structure 3f may for example be a closed and/or structured supporting layer of a certain thickness of approx. 0.01 cm to approx. 0.4 cm, preferably between approx. 0.02 cm and approx. 0.1 cm.

The base material 2 may be pre-heated 19 by means of a heat supplying means (not shown) prior to the printing step. Alternatively, the base material 2 may be heated throughout the 3D printing process. The heat supplying means may comprise a heated conveyor belt, a heat bulb, a hot air gun, an oven and/or an infrared radiation source and the like.

FIG. 6a is a top view of an example pre-made SU bag 1 with functional elements 3 being folded into a substantially two dimensional (2D) structure. In this configuration, functional elements 3 may preferably be 3D printed onto the SU bag 1. Alternatively or in addition, functional elements 3 are 3D printed onto a base material 2 which is a precursor of a SU bag 1, wherein the walls of the SU bag 1 are welded together in a stage after the functional elements 3 have been applied to the surface 2a of the base material 2.

In the present drawing, the SU bag 1 comprises a port 3b, possibly having a thread for connecting a pipe and/or a tube with the same. Further, the SU bag 1 comprises a set of holder elements 3d for holding a tube, a pipe and/or other elements for example. The holder elements 3d may be printed onto a field which may comprise at least one reinforcement element. The SU bag 1 also comprises a supported bottom having at least one reinforcement structure 3f to provide stability, particularly in an unfolded and filled state. The dashed lines indicate pre-folded edges which represent the edges of the SU bag 1 in an unfolded state.

The state in which the SU bag 1 is illustrated in FIG. 6a may be the state in which the SU bag 1 is purchased, shipped and/or stored. Preferably, the SU bag 1 is ready to be used in this state (particularly it is pre-sterilized), merely being required to be unfolded before use.

FIG. 6b is a perspective view of the pre-made SU bag 1 with functional elements being unfolded into a substantially 3D structure according to the example of FIG. 6a. The unfolding may be performed by pulling the edges apart from the layers and/or by pumping fluid (e.g. air) into the inside of the SU bag 1 via the at least one port 3b, for example. A tube 4b is connected to the port 3b of the SU bag 1 of FIG. 6b. The tube may be held by one of the holder elements 3d. The drawing reveals how the bottom of the SU bag 1 is supported along the edges and the bottom surface by means of the reinforcement structure 3f. The reinforcement structure 3f, and the port 3b, and the holder element 3d are made of rigid material. The side walls and the top wall of the SU bag 1 are made of flexible material. This combination of materials makes the SU bag 1 semi-flexible. The SU bag 1 is ready to be used (particularly pre-sterilized) and may be filled with a medium in the present state.

In the following, some general considerations are made, particularly for providing more possible features which may be combined with any of the example embodiment.

The term single-use container 1 is a general expression comprising the meaning of a bioreactor SU bag 1 or simply a specific form of a SU bag 1. The term bioreactor 1 may also comprise the meaning of a container for multiple uses, however essentially, the present embodiments mainly comprise a SU bag 1. For this reason, the same reference sign "1" is used for both expressions, bioreactor and SU bag.

A SU bag 1 and in particular a bioreactor 1 may generally be configured for single-use only, i.e. one use of the item (SU bag, particularly bioreactor 1) at a time, however not necessarily being restricted thereby. A single-use bag, particularly a single-use bioreactor may be also be used multiple times or over a certain period, depending on the user's requirements. It should be understood, that all embodiments disclosed herein may also be realized in a bioreactor 1 for multiple uses.

A functional element 3 is a substantially three dimensional (3D) element which provides a container, particularly a single-use bag with a certain function, as for example for realizing a measurement, a chemical and/or physical reaction, a and/or a processing step. In general, a functional element is not a substantially two dimensional (2D) element.

In more detail, functional part(s), particularly functional element(s) 3 can be component(s) for fluid transfer, such as ports 3b or flanges, for sensor(s) 4, such as sensor ports and/or sensor holders 3d, for stability, such as stiffeners and/or stiffening structures and/or pattern(s) 3f, for labelling, such as labels 3e or markers. Depending on the compatibility with the film material, being dependent from fusing parameters, and the function, 3D printable materials 5, from which at least a part of a functional element 3 can be formed, can be and/or can comprise one or more out of the following materials: PE (Polyethylene), HDPE (high-density polyethylene), LLDPE (linear low-density polyethylene), LDPE (low-density polyethylene), PP (Polypropylene), PC (Polycarbonate), TPE (Thermoplastic Elastomer), EVA (Ethylene-vinyl acetate), Fluoropolymers, PET (Polyethylene terephthalate), POM (Polyoxymethylene), ABS (Acrylonitrile butadiene styrene), PVC (Polyvinyl chloride), PLA (Polylactic acid), PA (Polyamide), PSU (Polysulfone), PES (Polyether sulfone), PEEK (Polyether ether ketone), Copolyesters, PMMA (Poly(methyl methacrylate)), PBI (phenylbenzimidazole sulfonic acid), PEI (Polyethylenimine), PPO (poly(phenylene oxide)), PS (polystyrene), PTFE (Polytetrafluoroethylene), PU (Polyurethane), silicone, acrylic resins, composites resins with fillers (e.g. PLA with glass fibers), any new material, which is developed and qualified as suitable for medical, pharmaceutical and biopharmaceutical applications, and composite materials out of at least one of the above mentioned materials. Other elements of the single-use bag 1, such as the base material 2, particularly a wall element 2a may also comprise or be composed at least in parts from the above list of materials.

The printable materials 5, from which at least a part of the functional element 3 is 3D printed, i.e. built and/or formed, can particularly comprise a thermoplastic material. A mixture or blend of multiple materials, particularly the said materials, may also be used as a printable material 5. Hence, a functional element 3 may be composed of a blend of at least two substantially different materials. This means that two materials can be mixed together before the step of printing the functional element 3. The functional element 3 comprises an essentially homogeneously mixed blend material. Alternatively, a functional element 3 may be formed in one portion from a first material and in another portion from another material, whereas the first and the second materials may be pure or blended or essentially homogeneously mixed. In other words, a blend of materials may be a transitioning filament, which is a part or portion of a functional element 3 and which is disposed, for example in direct contact with the base material 2 and from which the process of printing the functional element 3 is started or initiated.

For example, the printing of the functional element 3 may be started from a pure material, e.g. LDPE or any other material which fuses with the base material 2, and over the length of the filament and/or functional element 3 it blends into a second material, which is more suitable for another portion or part of the functional element 3, for example to build a sensor 4 or a stiffener 3f or another type of functional element 3. Preferably, a multi material filament, i.e. a functional element 3 having portions which comprise different materials, provide different material properties in different areas, particularly with respect to the diameter of the filament, e.g. core-sheath, or with respect to the length of the filament.

The single-use container may be a film based container. A film based container may be a container which comprises at least partially walls which comprise a thin, substantially 2D sheet.

SU bags 1, may be flexible or semi-rigid bioprocessing containers which are often composed of plastic sheets commonly called bag chamber films which may refer at least in parts to a base material 2. The film thickness can be, for example between approx. 40 μm and approx. 800 μm, preferably between approx. 80 μm and approx. 400 μm. The film can either be composed of mono- or multi-layers. Typically a film can comprise at least one out of: EVA, PE, PET, PA, EVOH (Ethylen-Vinylalkohol-Copolymer), Fluoropolymers, PP, TPE. SU bags 1, also called single-use container, may comprise semi-rigid or rigid single-use plastic containers, SU bags and/or containers for lab applications and SU bags and/or containers for food and beverage industries.

A flexible container is made of flexible material, such as a flexible sheet and/or a flexible film. A semi-flexible container is made partially of a flexible material and partially of a rigid material (e.g. one side or part of a side of the container). An example of a semi-flexible container is shown in FIG. 6b, with rigid elements 3b, 3d, 3f, and the side walls and the top wall made of flexible material.

Typical SU containers such as bags 1 may have a size between approx. 5 mL to approx. 5000 L, particularly between approx. 1 L to approx. 2000 L.

A container may particularly be a container for, production, storage, mixing, testing stability, validation, processing and/or transportation of any content (such as biopharmaceutical solutions). The container may particularly be a single-use container such as a single-use bioreactor, e.g. for the production of biopharmaceuticals. A single-use container may at least partly be flexible and/or semi-flexible, it may at least partly be a 2D- and/or 3D-structure.

LIST OF REFERENCE NUMERALS

1 Single-Use Container such as, Single-Use Bag and/or Bioreactor Single-Use Bag also abbreviated Single-Use (SU) Bag

2 Base Material, particularly Sheet being Essentially Two Dimensional and/or Wall of a Single-Use Bag
2a Surface of Base Material onto which Functional Element is Printed and/or Adhesion Surface
2b Opening of Base Material
3 3D Printed Functional Element
3a Handle being a Functional Element
3b Junction and/or Flange being a Functional Element
3c Port being a Functional Element
3d Sensor Holder with or without Sensor and/or Tube Holder being a Functional Element
3e Label and/or Reference Markers and/or Fiducials being a Functional Element
3f Structure, Pattern, Stabilizing, Stiffening and/or Reinforcement Element being a Functional Element
3g Layer of Printable Material as a Part of a Functional Element
4 Sensor
4a Tube and/or Pipe
5 Printable Material
5a Filament
5b Filament Roll
6 Portion of the Functional Element being Connected with the Base Element
7 Excess material of the Functional Element to be Removed/Cut Away
7a Excess material of the Functional Element being Removed/Cut Away
7b Grinded and/or Fractioned Excess material of the Functional Element
8 Means for Welding
9 Conventional Functional Element
9a Elongated Portion of Functional Element/Assembly Flange
9b Main Body of Conventional Functional Element
9c Excess Surface
10 Assembly Device
11 Three Dimensional (3D) Printing Device, Particularly a Printer (Extruder) Head
12 Means for Providing and Holding a Base Material, Particularly a Conveyor Belt
13 Heating Device
14 Roll of Base Material
14a Direction in which the Roll is Reeling Off
15 Means for Removing Excess Material of Functional Element and/or Base Material, for Example Laser Cutter
16 Means for Recycling Excess Material which has been Removed, particularly Cut Off
16a Mill for Reducing the Component Size of the Removed, particularly Cut Off Excess Material
17 System which either Provides the Removed, particularly Cut Off Material to the 3D Printer and/or which Manufactures new Base Material from Excess Material
18 Means for Heating
19 Heat
100 Method of Producing a Single-Use Bioreactor, particularly a Single-Use Bag
101 Step of Providing a Base Material
102 Step of (3D) Three Dimensional Printing
102a Step of 3D Printing a Functional Element onto a Surface of a Base Material
102b Step of Providing Heat Supply and Connecting the Functional Element with the Surface of a Base Material
103 Step of Removing and/or Cutting Away Excess Material and/or Portions of either the Functional Element and/or the Base Material U Upper Surface of Base Material, Particularly of a 2D Sheet L Lower Surface of Base Material, Particularly of a 2D Sheet $L_1$ Line Defining the Projection/Shadow of the Shape of the Functional Element onto the Base Material $L_2$ Line Defining the Projection/Shadow of the Shape of the Welding Machine onto the Base Material $d_1$ Length of the Assembly Flange/Elongated Portion Potentially Used in the present Embodiments $d_2$ Length of the Assembly Flange/Elongated Portion Needed for the Step of Welding (Conventional Techniques)

The invention claimed is:

1. A single-use container for use as a bioreactor, comprising:

a base material being a flexible material selected from the group consisting of a two-dimensional film, a stock sheet, a pre-cut bag, a pre-made bag, and a wall element of a bag or container; and at least one functional element being directly and permanently connected to the base material, wherein the at least one functional element comprises at least one printable material that is connected to the base material by heating the at least one printable material and simultaneously heating at least a portion of the base material during three-dimensional printing of the at least one printable material onto a surface of the base material, and wherein the at least one functional element comprises a port that is fused to the base material around an excess portion of the base material, and wherein the base material comprises an opening disposed within an interior region of the port, the opening being formed by removal of the excess portion of the base material after the port is connected.

2. The single-use container according to claim 1, wherein the at least one functional element further comprises at least one out of the following:

a flange, an inlet and/or outlet point, a sensor holder, a sensor or a part of a sensor, a window or a window frame, a tube holder, a handle, and a connector.

3. The single-use container according to claim 1, wherein the at least one functional element further comprises at least one out of the following:

a label, a substantially three-dimensional text, and a reference marker or fiducial.

4. The single-use container according to claim 1, wherein the at least one functional element further comprises a stabilizing element, stiffening element, and/or a reinforcement element.

5. The single-use container according to claim 1, wherein the at least one functional element further comprises an electronic component.

6. The single-use container according to claim 1, wherein the base material and/or the at least one functional element comprises at least one of: PE, EVA, ABS, PC, PMMA, PLA, PES, PSU, POM, PEEK, PEI, PPO, PP, PET, PS, PA, PTFE, PU, TPE, silicone, fluoropolymers, copolyesters, acrylic.

7. The single-use container according to claim 1, wherein the at least one printable material is printed by a three dimensional printing technique comprising a fused filament fabrication, a drop-by-drop application of the printable material, and/or a layer-by-layer application of the printable material.

8. The single-use container according to claim 7, wherein the three dimensional printing technique further comprises printing from one or more of nanoparticle ink, spraying atomized metal, melting a metal powder, and aerosol jetting an electronic component.

9. A method of producing a single-use container by producing at least one functional element and connecting the at least one functional element with a base material of the container, comprising the steps of:

providing the base material, the base material being a flexible material selected from the group consisting of a two-dimensional film, a stock sheet, a pre-cut bag, a pre-made bag, and a wall element of a bag or container;

three-dimensional printing of the at least one functional element from a printable material on a surface of the base material; and connecting at least a portion of the at least one functional element with at least a portion of the base material by supplying heat to the printable material and the base material simultaneously to and/or prior to at least an interval of the step of three dimensional printing, wherein the at least one functional element comprises a port that is fused to the base material around an excess portion of the base material, and removing the excess portion after the port is fused to the base material to define an opening within an interior region of the port.

10. The method according to claim 9, wherein the step of supplying heat comprises the step of pre-heating the base material.

11. The method according to claim 9, wherein the step of three dimensional printing of the at least one functional element comprises a step of printing from printable material, at least one of: acrylics, EVA, ABS, PC, PE, PMMA, PLA, PES, POM, PEEK, PEI, PP, PS, PTFE.

12. The method according to claim 9, wherein the step of three dimensional printing comprises the step of printing from a nanoparticle ink and/or spraying atomized metal and/or melting a metal powder and/or aerosol jetting an electronic component.

13. The method according to claim 9, further comprising the step of removing a portion of the base material and/or removing an excess portion of the at least one functional element.

14. The method according to claim 9, wherein the three-dimensional printing of the at least one functional element comprises a fused filament fabrication, a drop-by-drop application of the printable material, and/or a layer-by-layer application of the printable material.

15. The method according to claim 9, further comprising removing excess material from either the at least one functional element and/or the base material; and at least partly recycling the excess material being removed by reusing it in the three dimensional printing step and/or in a step of manufacturing the base material.

* * * * *